United States Patent [19]

Ramachandran et al.

[11] Patent Number: 4,764,635
[45] Date of Patent: Aug. 16, 1988

[54] AROMATIZATION PROCESS

[75] Inventors: Venkataraman Ramachandran; David M. Mohr, both of Baton Rouge, La.

[73] Assignee: Ethyl Corporation, Richmond, Va.

[21] Appl. No.: 896,461

[22] Filed: Aug. 14, 1986

[51] Int. Cl.$^4$ ............................................. C07C 121/62
[52] U.S. Cl. ..................................... 558/423; 585/410
[58] Field of Search ........................... 558/423, 410 B; 855/410

[56] References Cited

U.S. PATENT DOCUMENTS 4,237,070 12/1980 Patterson et al. ..................... 260/580
4,590,010 5/1986 Ramachandran et al. ......... 558/341

FOREIGN PATENT DOCUMENTS 0032019 7/1981 European Pat. Off. .

OTHER PUBLICATIONS

Bianchi et al., *Chem. Abs.*, vol. 92, No. 8, pp. 666–667, 92:76372t, (1980).

*Primary Examiner*—Anton H. Sutto
*Attorney, Agent, or Firm*—Patricia J. Hogan

[57] ABSTRACT

A hydroaromatic compound is aromatized by heating it at about 100°–300° C. in the presence of a hydrogen acceptor. In a preferred embodiment of the invention, the hydroaromatic compound is a dihydronaphthalene bearing an electron-withdrawing substitutent, e.g., a cyanodihydronaphthalene.

5 Claims, No Drawings

AROMATIZATION PROCESS

FIELD OF INVENTION

This invention relates to the aromatization of hydroaromatic compounds.

BACKGROUND

As disclosed in Morrison and Boyd, *Organic Chemistry*, Third Edition, Allyn and Bacon, Boston, 1973, pp. 974–976, and March, *Advanced Organic Chemistry*, Second Edition, McGraw-Hill, New York, pp. 1077–1078, it is known that hydroaromatic compounds can be aromatized in various ways. However, the known aromatization techniques are generally characterized by one or more disadvantages, such as high cost, the need for fairly severe conditions, the lack of sufficient ease in removing the aromatizing agent from the product, etc.

U.S. Pat. No. 4,590,010 (Ramachandran et al.-I) teaches that 6-alkoxy-1-cyano-3,4-dihydronaphthalenes can be aromatized by known techniques, such as by dehydrogenation in the presence of a palladium-on-carbon catalyst.

Copending application Ser. No. (880,070) (Ramachandran et al.-II), filed June 30, 1986, teaches that hydroaromatic compounds, including the 6-alkoxy-1-cyano-3,4-dihydronaphthalenes of Ramachandran et al.-I, can be aromatized by the use of a base.

SUMMARY OF INVENTION

An object of this invention is to provide a novel aromatization process.

Another object is to provide such a process which is effective in the absence of an aromatizing agent.

These and other objects are attained by heating a hydroaromatic compound at about 100°–300° C. in the presence of a hydrogen acceptor so as to aromatize the hydroaromatic compound.

DETAILED DESCRIPTION

The compound that is aromatized in the practice of the present invention is a hydroaromatic compound, i.e., a compound which, as defined by Morrison and Boyd, contains the carbon skeleton of an aromatic system but too many hydrogen atoms for aromaticity. Such compounds include completely saturated compounds, such as cyclohexane, decalin, etc., but are generally compounds wherein the ring to be aromatized contains at least one double bond, e.g., cyclohexene, dihydrobenzene, etc., and/or is fused to an aromatic ring, e.g., tetralin, methoxytetralones, dihydroquinolines, dihydroisoquinolines, dihydroanthracenes, dihydrophenanthrenes, etc.

In a preferred embodiment of the invention, the hydroaromatic compounds are dihydroaromatic compounds, especially dihyronaphthalenes, and most especially such compounds bearing an electron-withdrawing substituent, such as $-N(CH_3)_3 +$, $-NO_2$, $-CN$, $-SO_3H$, $-COOH$, $-COOR$, $-CHO$, $-COR$, or X, wherein R is hydrocarbyl (e.g., an alkyl, cycloalkyl, aryl, alkaryl, or aralkyl group, generally such a group containing 1–10 carbons) and X is halo (i.e., chloro, bromo, fluoro, or iodo). Such compounds include, e.g., trimethylammoniumdihydronaphthalene hydrochlorides; nitro- and dinitrodihydronaphthalenes; cyanodihydronaphthalenes; dihydronaphthalenesulfonic acids; dihydronaphthoic acids; methyl, ethyl, propyl, butyl, pentyl, hexyl, phenyl, benzyl, and tolyl dihydronaphthoates; dihydronaphthaldehydes; methyl, ethyl, propyl, butyl, pentyl, hexyl, phenyl, benzyl, and tolyl naphthyl ketones; bromo-, chloro-, fluoro-, and iododihydronaphthalenes, etc., including such compounds which bear other substituents, such as additional electron-withdrawing groups or electron-donating groups, e.g., alkyl, alkoxy, amino, trifluoromethyl, etc.

Substituents on the ring, although generally inert, may be reactive, e.g., nitro. However, it should be kept in mind that a reactive substituent can undergo reaction during the aromatization and that its presence can therefore influence the particular reaction conditions employed, as well as the product formed. Thus, e.g., the presence of a reducible substituent can obviate the need for using an additional hydrogen acceptor.

Since the objective of the invention is not to prepare any particular aromatic compound but to provide a more general, economically-attractive process for the aromatization of hydroaromatic compounds, there are no generally-preferred starting materials in the usual sense. The preferred starting material in any instance will depend on the particular aromatic compound desired. However, as indicated above, there are factors that can make one precursor of a given aromatic compound preferable to another, e.g., cost, availability or the relative ease with which it can be prepared, the relative ease with which it can be aromatized, etc. Thus, e.g., considering the last of these factors, a dihydroaromatic compound is preferred to a tetrahydroaromatic compound, and it is easier to aromatize a ring that is fused to an aromatic ring.

Because of the utility of the products and the ease with which the precursors can be aromatized, a preferred embodiment of the invention is the aromatization of 3,4-dihydronaphthalenes having an electron-withdrawing substituent, especially a cyano group, in the 1-position. Exemplary of such dihydronaphthalenes are 1-cyano-3,4-dihydronaphthalene, 6-alkoxy-1-cyano-3,4-dihydronaphthalenes wherein the alkoxy group preferably contains 1–6 carbons, 6-alkyl-1-cyano-3,4-dihydronaphthalenes wherein the alkyl group preferably contains 1–6 carbons, the 5-bromo, 5-iodo, and 5-trifluoromethyl derivatives of the alkoxy and alkyl compounds, the corresponding compounds wherein the 1-substituent is one of the other electron-withdrawing substituents mentioned above, etc. The cyano compounds, especially those bearing a methoxy or other alkoxy substituent in the 5-position, are of particular interest because of their utility in a modification of the process of Ramachandran et al.-I, the teachings of which are incorporated herein by reference.

As mentioned above, the hydrogen acceptor may be the hydroaromatic compound itself when that compound contains at least one reducible group. However, the acceptor is more commonly a separate compound, generally a nitro compound, and preferably a nitroarene capable of serving as a solvent. Exemplary of utilizable hydrogen acceptors are oxygen; sulfur; selenium; dihalobenzenes; olefins, such as hexene, dodecene, ethylene, styrene, etc., nitroalkanes, such as nitroethane, 1-nitrohexane, 3-nitro-2,2-dimethylbutane, 2-nitro-2-methylpentane, etc., and nitroarenes, such as nitrobenzene, 2-, 3-, and 4-nitrotoluenes, 2- and 4-nitroethylbenzenes, 2-nitro-1,3,5-trimethylbenzene, nitronaphthalenes, dinitrobenzenes, dinitronaphthalenes, etc., with nitrobenzene being especially preferred. The amount of hydrogen acceptor employed should be at least an equivalent amount and can be much higher, since there is no maximum to the amount that may be used.

To permit better control of the reaction, it is preferable to conduct the aromatization in the presence of a solvent. When a solvent is employed, it may be any normally liquid organic material capable of solvating the hydroaromatic compound, but it is preferably a compound capable of serving both as a solvent and as a hydrogen acceptor. It is most preferably a nitroarene solvent such as those mentioned above, especially nitrobenzene.

In conducting the aromatization, a pure or crude hydroaromatic compound is intimately contacted with the hydrogen acceptor and heated at about 100°–300° C., preferably about 150°–250° C., until the desired degree of aromatization has occurred. The time required for the reaction varies with the degree of aromatization desired, the relative ease with which the hydroaromatic compound is aromatized, and the particular temperature employed; but a fairly typical reaction time is about 4–24 hours.

After completion of the reaction, the aromatic product may be recovered by conventional means and/or converted to a desired derivative, such as the pharmaceutical materials of U.S. Pat. No. 4,439,617 (Sestanj et al.).

The invention is advantageous as a commercially-attractive process for aromatizing hydroaromatic compounds and is especially advantageous as a means of aromatizing 3,4-dihydronaphthalenes which are useful as precursors of the pharmaceuticals taught by Sestanj et al.

The following examples are given to illustrate the invention and are not intended as a limitation thereof. Unless otherwise specified, quantities mentioned in the examples are quantities by weight.

EXAMPLE I

A solution of 18.5 parts of 6-methoxy-1-cyano-3,4-dihydronaphthalene (MCDN) in about 120 parts of nitrobenzene was gently refluxed at 210° C. for 8 hours. Quantitative GC analysis of the resultant reaction mixture showed the presence of 17.9 parts (a 98% yield) of 6-methoxy-1-cyanonaphthalene (MCN).

EXAMPLE II

A solution of 7.4 parts of MCDN in a mixture of 55.5 parts of nitrobenzene and 37.1 parts of toluene was divided into two portions, each of which was heated to 148° C. over a period of 5.25 hours to boil off the toluene and then cooled. The portions were combined, and analysis showed that 3.5% of the MCDN had been converted to MCN. The combined portions were then heated to 215° C. over a period of 9 hours with simultaneous stripping of solvent, and the temperature began to fluctuate in the range of about 145°–215° C. for almost 14 hours because of problems with the heating medium. Analyses showed that the conversion of MCDN to MCN was 47% prior to the temperature fluctuation period and 99.5%

EXAMPLE III

Following the same general procedure as in Example II, two portions of a solution of 12 parts of MCDN in a mixture of 80.4 parts of nitrobenzene and 7.6 parts of toluene were concentrated, cooled, combined, heated to 210° C. over a period of 14 hours with simultaneous removal of solvent, and then maintained at about 206°–212° C. for 10 hours, Analyses showed that the conversion of MCDN to MCN was 2% after the concentration step and 99.7% at the end of the reaction.

EXAMPLE IV

Following the same general procedure as in Examples II and III, a nitrobenzene/toluene solution of MCDN was divided into two portions, which were then concentrated, combined, and heated at temperatures in excess of 200° C. until aromatization was complete. Concentration of the first portion of the solution was accomplished by heating it to 190° C. over a period of almost 12 hours; concentration of the second portion was accomplished by heating it to 200° C. over a period of close to 22 hours. Analysis of the combined portions showed that the concentration temperatures converted about 30% of the MCDN to MCN.

EXAMPLE V

A crude nitrobenzene/toluene solution of about 6.2% MCDN and 4.4% MCN was heated to 210° C. over a period of about 20 minutes, during which time the toluene was removed. The resulting mixture was then held at 210° C. for about four hours, after which vacuum distillation gave MCN in an isolated yield of about 96%.

It is obvious that many variations may be made in the products and processes set forth above without departing from the spirit and scope of this invention.

We claim:

1. A process which comprises heating a 6-alkoxy-1-cyano-3,4-dihydronaphthalene at about 100°–300° C. in the presence of a hydrogen acceptor so as to aromatize the dihydronaphthalene.

2. The process of claim 1 wherein the hydrogen acceptor is a nitroarene solvent.

3. The process of claim 2 wherein the hydrogen acceptor is nitrobenzene.

4. The process of claim 1 wherein the temperature is about 150°–250° C.

5. A process which comprises heating a 6-alkoxy-1-cyano-3,4-dihydronaphthalene at about 150°–250° C. in the presence of nitrobenzene so as to aromatize the dihydronaphthalene.

* * * * *

UNITED STATES PATENT AND TRADEMARK OFFICE
CERTIFICATE OF CORRECTION

PATENT NO. : 4,764,635

DATED : August 16, 1988

INVENTOR(S) : Venkataraman Ramachandran et al

It is certified that error appears in the above-identified patent and that said Letters Patent is hereby corrected as shown below:

Column 4, line 4, reads "99.5%" and should read -- 99.5% at the end. --.

Signed and Sealed this

Thirteenth Day of December, 1988

Attest:

DONALD J. QUIGG

*Attesting Officer*  *Commissioner of Patents and Trademarks*